United States Patent
Poulsen et al.

(10) Patent No.: US 7,367,965 B2
(45) Date of Patent: May 6, 2008

(54) OSTOMY APPLIANCE WITH MULTIPLE OPENINGS FOR PREVENTING FILTER INPUT BLOCKAGE

(75) Inventors: Lars Bo Poulsen, Helsingoer (DK); Per Ole Nielsen, Broenshoei (DK)

(73) Assignee: Coloplast A/S, Humlebaek (DK)

( * ) Notice: Subject to any disclaimer, the term of this patent is extended or adjusted under 35 U.S.C. 154(b) by 143 days.

(21) Appl. No.: 10/499,823

(22) PCT Filed: Feb. 26, 2003

(86) PCT No.: PCT/DK03/00122

§ 371 (c)(1),
(2), (4) Date: Jul. 6, 2004

(87) PCT Pub. No.: WO03/071997

PCT Pub. Date: Sep. 4, 2003

(65) Prior Publication Data
US 2005/0085779 A1    Apr. 21, 2005

(30) Foreign Application Priority Data
Feb. 28, 2002 (DK) .............................. 2002 00317

(51) Int. Cl.
*A61M 1/00* (2006.01)
*A61F 5/44* (2006.01)

(52) U.S. Cl. .................... 604/333; 604/322; 604/324; 604/332

(58) Field of Classification Search ........ 604/332–334, 604/337, 327, 277; 600/32; 128/887
See application file for complete search history.

(56) References Cited

U.S. PATENT DOCUMENTS

| 4,211,224 | A | | 7/1980 | Kubach et al. |
| 4,367,732 | A | | 1/1983 | Poulsen et al. |
| 4,427,425 | A | * | 1/1984 | Briggs et al. .................. 96/12 |
| 4,439,191 | A | * | 3/1984 | Hogan ......................... 604/332 |
| 4,449,970 | A | | 5/1984 | Bevan et al. |
| 4,938,749 | A | | 7/1990 | Jensen |
| 4,938,750 | A | | 7/1990 | Leise, Jr. |
| 5,051,259 | A | | 9/1991 | Olsen et al. |

(Continued)

FOREIGN PATENT DOCUMENTS

EP    0235928 A1 *   1/1987

(Continued)

*Primary Examiner*—Tatyana Zalukaeva
*Assistant Examiner*—Melanie J. Hand
(74) *Attorney, Agent, or Firm*—Jacobson Holman PLLC

(57) ABSTRACT

An ostomy appliance with a front wall and a rear wall of flexible material forming a bag, the rear wall having an opening into the bag by which waste material can enter the bag. The bag has two or more vents through which gas may escape from the bag and a filter device covering each vent. Each filter device has gas inlet and outlet openings in communication with a respective filter body so that in use gas flows through the filter device from the inlet opening through the filter body to the outlet opening. The inlet openings communicate with the inner space of the bag and are located near the border of the bag, being spaced at an angle of at least 45 degrees along radii of a circle of reference having a perimeter concentric with the waste opening of the bag.

18 Claims, 4 Drawing Sheets

U.S. PATENT DOCUMENTS

| | | | |
|---|---|---|---|
| 5,690,623 A | * | 11/1997 | Lenz et al. ................ 604/333 |
| 5,714,225 A | | 2/1998 | Hansen et al. |
| 5,800,415 A | | 9/1998 | Olsen |

FOREIGN PATENT DOCUMENTS

| | | |
|---|---|---|
| EP | 0 235 928 | 9/1987 |
| EP | 0 443 728 | 8/1991 |
| EP | 1 051 955 | 11/2000 |
| GB | 1571382 | 7/1980 |
| GB | 1586182 | 3/1981 |
| GB | 2 311 014 | 9/1997 |
| WO | 83/02890 | 9/1983 |
| WO | 91/01118 | 2/1991 |
| WO | 91/01119 | 2/1991 |
| WO | 94/18919 | 9/1994 |
| WO | 98/44880 | 10/1998 |
| WO | WO 9844880 A1 * | 10/1998 |
| WO | 99/66859 | 12/1999 |

* cited by examiner

OSTOMY APPLIANCE WITH MULTIPLE OPENINGS FOR PREVENTING FILTER INPUT BLOCKAGE

This is a nationalization of PCT/DK03/00122 filed Feb. 26, 2003 and published in English.

BACKGROUND OF THE INVENTION

1. Field of the Invention

The present invention relates to an ostomy appliance comprising a deodorising filter, in particular ostomy bags.

In connection with surgery for a number of diseases in the gastro-intestinal tract a consequence is, in many cases, that after a colostomy, an ileostomy or an urostomy, the patient is left with a stoma in the abdominal wall for the discharge of the effluents or waste products of the body, which are conveyed through the colon, the ileum or the ureter. The discharge of visceral contents including intestinal gases cannot be regulated at will, and for that purpose the opening may be closed with a closure means, e.g. a tampon or a magnetic closure, or the patient will have to rely on an appliance to collect the material emerging from such opening in the form of a receiving bag which is later emptied and/or discarded at suitable times.

Ostomy appliances are well known. Such appliances may be two-piece or one-piece appliances. In both types of appliances, an adhesive wafer is attached to the wearer's skin. In case of a one-piece appliance, a receiving member or bag is attached to the adhesive wafer. In case of a two-piece appliance, the adhesive wafer forms part of a body side member and a receiving bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side member is left in place up to several days, and only the receiving bag attached to the body side member is replaced.

The discharge of flatus, measured in volume, may exceed the discharge of solid and liquid faecal matter by many hundred percent and therefore there is usually the need for the continuous or frequent venting of the intestine or the collecting bag. Normally the outflowing flatus is deodorised with a suitable filter. Commonly the active filter is powdered active carbon, which absorbs $H_2S$ being the principal component of the smell of flatus.

In connection with the use of filters there is a need of measures for effectively preventing blocking of the inlet opening of filters of ostomy appliances. When the inlet opening of the filter is blocked, the gas discharged into the ostomy appliance cause ballooning of the bag which is highly undesirable for several reasons. Ballooning will be embarrassing for the user as the bag will bulge and there is an increased risk of leakage which is unacceptable for the user.

2. Description of the Related Art

Various constructions of filters for ostomy appliances are known. In the state of the art, the filters are designed so as to obtain a high security of deodorisation of the flatus by securing that there is no by-pass by which the flatus may circumvent the filter, and some measures have been discussed with respect to obtaining a better security against blocking of the inlet of the filter by solid discharged visceral content.

Thus, European Patent No. 0 235 928 discloses that a filter may be rendered suitable for use with ileostomy equipment when the filter wall adapted to face the source of intestinal gas is covered by a layer of sheet material, preferably plastic sheet material connected to the filter walls and, inside the periphery of this connection, provided with openings such as slits for the passage of intestinal gas. However, such slits may open if the pressure is high giving free flow of gas and liquid through the layer of sheet material. As an additional or alternative measure, it is proposed to provide the filter housing on the surface adapted to face the source of intestinal gas with a layer of liquid-absorbing material.

EP patent No. 0 443 728 B1 discloses a bag for receiving discharge from the human body comprising a filter and an intervening membrane covering the inlet opening of the filter, said intervening membrane being gas permeable but not liquid permeable. It is mentioned that the membrane may comprise a polyester film bonded to a PTFE film and that such membrane showed no leakage of water. There is no indication of security against leaking when exposed for discharge from an ileostomy or liquids from a colostomy.

Published International Patent Application WO 98/44880 discloses a filter for covering a vent of an ostomy appliance, said filter comprising an elongated, substantially flat filter body of a porous filter material interposed between gas and liquid impervious walls which are sealed to the body along its longitudinal side edges; gas inlet and outlet openings being provided in communication with the filter material adjacent to its respective longitudinal end regions, wherein both of the gas and liquid impervious walls are sealed to the upper and lower surfaces of the filter body, wherein the inlet opening is covered by a hydrophobic sheet, wherein the inlet opening is covered with a microporous oleophobic membrane and wherein a foam material is covering the inlet opening of the vent. Such arrangement shows improved resistance against wetting and blocking of the filter caused by humidity or other liquid constituents of the visceral contents of an ostomy collection bag and, at the same time, shows improved resistance against clogging of the filter.

U.S. Pat. No. 4,938,750 discloses a medical device comprising a collection receptacle in the form of a thin walled pouch, a member affixed to the pouch wall comprising a plurality of isolated gas passages, each constituting a vent, separate deodorising filter means in each one of said passages and means for obstructing the flow through all but a selected one of said passages. The passages and the filter means are located on a member which is preferably aligned with the stoma receiving opening. With this location, however, due to the close localisation of the filters, the risk of blocking of all filters is roughly of the same magnitude as in case of one filter. The risk of blocking the filter disclosed in U.S. Pat. No. 4,938,750 is relatively high due to the localisation of the filters aligned with the stoma receiving opening.

EP patent application No. 1 051 955 A2 discloses a bag for receiving discharge from the human body, said bag having a distal and a proximal wall one of which has a gas venting aperture and a filter for deodorising gas vented through the venting aperture wherein a filter package may be located at one or both sides of the bag wall. EP patent application No. 1 051 955 A2 does not disclose more filters having separate inlet openings communicating with the inner space of the bag.

U.S. Pat. No. 4,938,749 discloses a filter housing for mounting on an ostomy pouch, said housing having a base member having a central gas inlet passageway and three exit passageways radially offset from the inlet passageway and said housing further having a cover member having a recess with three connecting passageways which extend in a radial direction a distance from the central axis of the cover member greater than the distance between exit passageways and the axis of the base member, said base member being able to move between a first position in which said connecting channel aligns with said exit passageway and a second position at which said connecting channel is remote from said exit passageway. Thus, U.S. Pat. No. 4,938,749 does not disclose more filters having separate inlet openings communicating with the inner space of the bag.

However, it has been found that even when using such filters there is a risk, especially at night when ostomates turn in bed, of directly pressing faeces in the receiving bag against the inlet opening(s) of the filter and that the pressure may be sufficiently high to pass the viscerous material through a foam material covering the inlet opening of the vent and to cause a blocking of a microporous oleophobic covering the inlet opening of the vent.

Thus, there is still a need of measures for effectively preventing blocking of the inlet opening of filters of ostomy appliances.

It has now been found that it is possible to reduce the risk of blocking of the inlet opening of filters of ostomy appliances in a manner that almost eliminates the risk and, at the same time, is simple to carry out in industrial practice.

Thus, it has been found that the above drawbacks can be avoided by improving the geometry of the passage to the inlet opening of the filter.

SUMMARY OF THE INVENTION

BRIEF DESCRIPTION OF THE DRAWINGS

The invention is disclosed more in detail with reference to the drawings in which.

DETAILED DESCRIPTION OF THE PRESENT INVENTION

Figure 1:
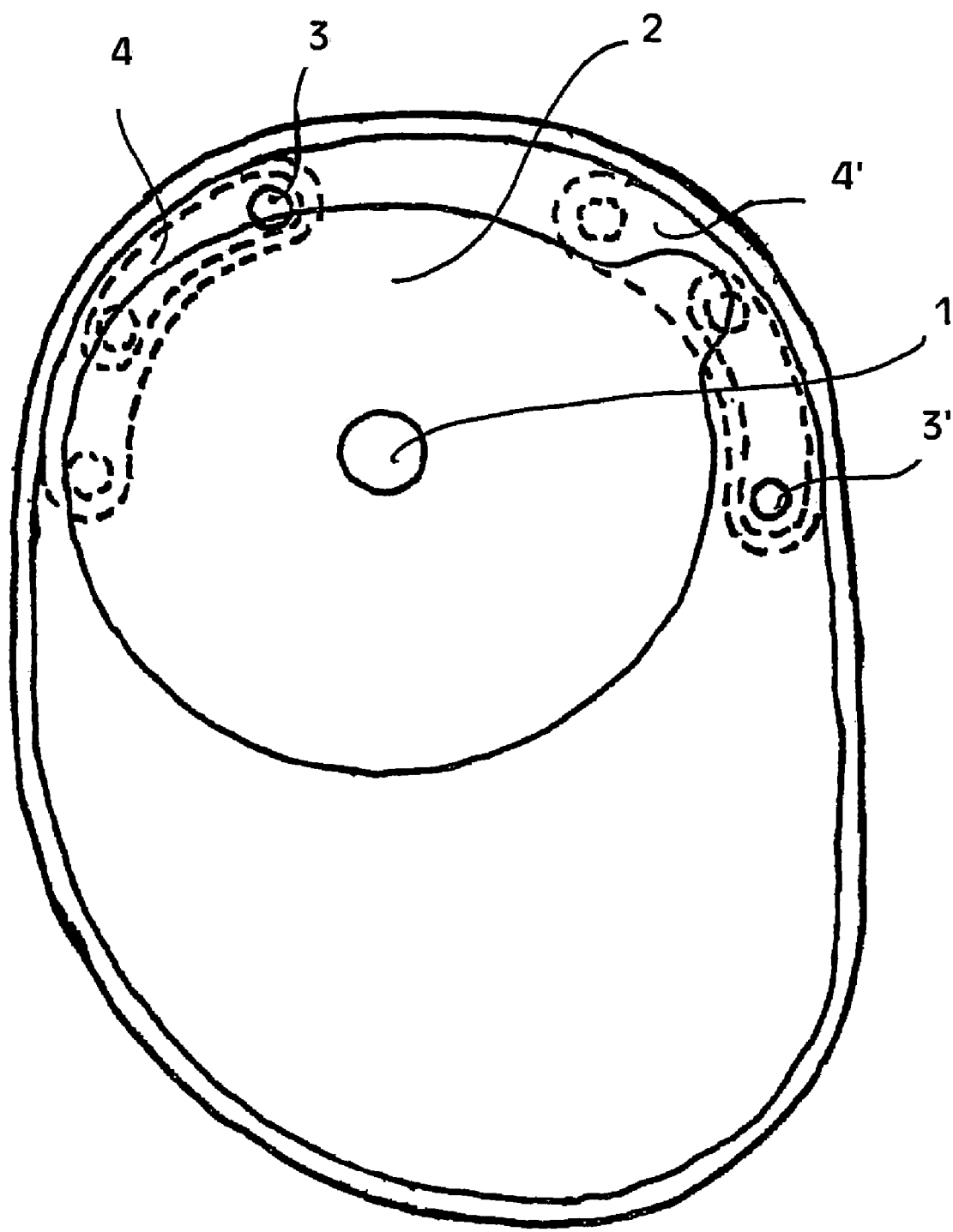
FIG. 1 shows one embodiment of an ostomy appliance of the invention.

In its broadest aspect the invention relates to an ostomy appliance comprising a front wall and a rear wall of flexible material forming a bag, the rear wall having an opening into the bag by which waste material can enter the bag, said bag having two or more vents through which gas may escape from the bag and having a filter device covering each vent.

In one embodiment the present invention relates to an ostomy appliance comprising a front wall and a rear wall of flexible material forming a bag, the rear wall having an opening into the bag by which waste material can enter the bag, said bag having two or more vents through which gas may escape from the bag and having a filter device covering each vent, said filter device being provided with gas inlet and outlet openings in communication with at least one filter body, the arrangement being so that in use gas flows through the filter device from the inlet opening to the outlet opening, such gas flow being confined to said filter body, wherein one of the walls of the ostomy appliance is provided with at least two separate filter devices having separate inlet openings communicating with the inner space of the bag and wherein the inlet openings of the filter devices are located near the border of the bag.

The risk of blocking of the inlet opening of the filter is significantly reduced by the presence of two separate filter devices having separated inlet openings located near the border of the bag and communicating with the interior of the bag. Thus, material present in the bag is hampered from entering, at the same time, both pathways leading to the inlet openings of the filter devices which has been found nearly to eliminate the risk of blocking of both filters by directly pressing the contents of the bag against the inlet openings of the filters e.g. when a lying person turns. e.g. in bed.

Furthermore, the risk of ballooning of a bag due to incidental high discharge of gas is reduced considerably when using two filter devices as the venting area of the bag is then doubled if identical filter devices are used.

The appliances of the invention may be made from elements already used in the manufacture of ostomy appliances by applying an extra filter device and it is also simple to establish a desired distance between the inlet openings of the filters to minimise the risk of blocking.

The effect of having two separate filters openings is improved when the separated inlet openings of the filters are spaced a certain distance from each other, a certain effect being found already at a distance of at least 15 mm, the effect increasing with increasing distance until a distance comparable to the width of the bag is reached. It is preferred, that the distance is at least 50 mm and it is especially preferred, that the distance corresponds to 90% or more of the width of the bag for which the filter device is intended.

It provides a pronounced effect when the inlet openings of the filter devices are spaced at an angle of at least 45 degrees essentially along radii of a circle of reference having a perimeter concentric with the inlet opening of the bag, and it is preferred that the inlet openings are spaced at an angle of at least 90 degrees.

It is especially preferred that the inlet openings are spaced at an angle of at least 135 degrees which will be very suitable taking into account the shape of a bag where the filter device is to be placed but angles of up to 180 degrees are considered suitable for the purpose of the present invention.

The inlet openings of the filter devices of an ostomy appliance are generally located near the border of the bag, preferably between the border of the bag and the perimeter of the opening into the bag by which waste material can enter the bag in order to reduce the risk of such material directly coming Into contact with the inlet openings of the filter devices and maybe blocking the same. The inlet openings are preferred located as close to the border as possible, suitably less than 3 centimeters from the border, e.g. between 0.5 and 2 centimeters and more suitably about 1-1.5 centimeters from the border.

Filter devices for use in accordance with the present invention may be any filter device known per se for ostomy purposes and are suitably devices of the kind disclosed in GB 1 571 382 or preferably in WO 98/44880. Such filter devices are suitably of generally circular or elongated shape. It is considered an embodiment of the invention to use more than one kind of filter devices in one bag, e.g. a circular and an elongated filter device.

It is preferred that the filter devices have border lines being a part of a circle which renders it easier to locate the filters at the top border of the bag.

Elongated filter devices may be placed in a bag of the invention in any desired and suitable configuration as long as the inlet openings fulfil the above-mentioned criteria.

Thus, elongated filter devices may be located generally along the border of the bag or having the longest extent generally in an angle thereto. Thus, an elongated filter device may be placed extending along a line forming an angle from about 0 to about 90 degrees (i.e. along a radius) with the tangent of the border of the bag nearest the inlet opening of the filter device.

When using elongated filter devices it is especially preferred that at least the part of the top of the bag wherein the filters are secured has a border line being a part of a circle having the same diameter as the filter devices allowing a localisation of the filters inside the bag very near to the border of the bag.

When all of the top of the bag has a border line being a part of a circle having the same diameter as the filter devices it is possible to locate elongated filters freely along the inner rim of the bag.

In one preferred embodiment of the invention, the filter devices are located at opposite sides of the vertical centre line of the bag.

In another preferred embodiment of the invention, elongated filter devices are located end to end at the top of the bag, preferably having their inlet openings located opposite the adjacent ends.

Two elongated filter devices each having only one inlet opening which is not centrally located may be arranged in a "heads-to tail" relationship or in such a relationship that their inlet openings are located in the ends nearest the other filter device or preferably in the ends being most distant from the other filter device.

In another embodiment the present invention relates to an ostomy appliance comprising a front wall and a rear wall of flexible material forming a bag, the rear wall having an opening into the bag by which waste material can enter the bag said bag having two or more vents through which gas may escape from the bag and having a filter device covering each vent, said filter device being provided with gas inlet and outlet openings in communication with at least one filter body, the arrangement being so that in use gas flows through the filter device from the inlet opening to the outlet opening, such gas flow being confined to said filter body, wherein each of the walls of the ostomy appliance is provided with at least one vent and a filter device having an inlet opening communicating with the inner space of the bag and wherein the Inlet openings of the filter devices are located near the border of the bag.

When the filters are located one in each wall, the risk of pressing the contents of the bag against both inlet openings is further reduced.

Preferred embodiments thereof as well as preferred location of the filter devices in this embodiment correspond to the ones stated above for ostomy appliances having two vents in the same wall.

It is preferred that an ostomy appliance of the invention comprises two vents each covered by a filter device.

The filter devices may in accordance with the invention be placed at the inner side or at the outer side of the ostomy appliance as found suitable for the application in question considering the intended use. The ostomy receiving bag according to the invention may be adapted for use together with an ostomy body side member (2-piece appliance) wherein the receiving bag is provided with coupling means for releasable securing to matching coupling means placed on the ostomy body side member and wherein the inlet opening is adapted for alignment with a hole of the ostomy body side member for receiving a stoma.

The ostomy receiving bag according to the invention may, as an alternative, be adapted for use directly (1-piece appliance) in which case the bag is provided with an adhesive wafer for securing the receiving bag to the user's skin, said bag and wafer having an inlet opening for receiving a stoma.

The receiving bag itself comprising front and rear walls sealed together along the rim and provided with an inlet opening may be made in analogy with and from materials conventionally used for the preparation of ostomy appliances.

Such materials are suitably films composed of any suitable material which is heat sealable and sufficiently impervious for unpleasant odours such as polyolefin films or combinations of such films, e.g. polyethylene or a coextrudate of polyethylene and polyvinylidene.

In accordance with a preferred embodiment of the invention, the receiving bag is an open bag of the kind disclosed in WO 99/66859 having two filter devices.

An ostomy body side member for use together with an ostomy receiving bag according to the invention may be produced from standard materials normally used for preparation of disposable ostomy and wound and incontinence devices.

Thus, the adhesive wafer for a body side member or of a 1-piece ostomy appliance bag according to the invention may be made from a medical grade barrier adhesives known in the such as the formulation being disclosed, for example in U.S. Pat. Nos. 4,367,732, 5,051,259 or 5,714,225. For a 2-piece ostomy appliance according to the invention the body side member and the receiving bag are provided with matching coupling means.

The coupling means for use in connection with the present invention may be any suitable coupling means known per se for coupling of ostomy base plates to ostomy collecting bags, e.g. a mechanical coupling such as matching coupling rings such as the coupling rings disclosed in WO 91/01118 and WO 91/01119 or WO 94/18919 or matching flanges for adhesive connection of the type disdosed in U.S. Pat. No. 5,800,415.

DESCRIPTION OF THE PREFERRED EMBODIMENTS

The invention is now explained more in detail with reference to the drawings showing preferred embodiments of the invention. However, it should be understood that the detailed description and specific examples, while indicating preferred embodiments of the invention, are given by way of illustration only, since various changes and modifications within the spirit and scope of the invention will become apparent to those skilled in the art from this detailed description.

Reference is made to FIG. 1 of the drawings showing an embodiment of an ostomy appliance of the invention, seen from the side facing the user, which shows a preferred one-piece embodiment of an ostomy appliance of the invention comprising a front wall and a rear wall of a flexible material, said rear wall having an opening 1 into the bag by which waste material can enter the bag. The appliance has an adhesive wafer 2 for adhering to the user's skin. Furthermore, the appliance has vent openings 3,3', for clarity shown in full-drawn line even if hidden behind the wafer, on the front wall through which gas may escape from the bag, said vent opening being covered of two filter devices 4,4' wherein gas inlet and outlet openings are provided in communication with the filter body, the arrangement being so that in use, gas flows through the filter from the inlet opening to the outlet opening, such gas flow being confined to said filter body. The filter devices are preferably secured to the wall by welding in a manner known per se.

The presence of a hydrophobic and oleophobic membrane in the filter devices reduces the risk of wetting of the filter material and a foam material improves the security against blocking of the inlet opening to the filter. This effect is further enhanced by the application of two filter devices. Thus, the risk that material present in the bag enters, at the same time, both or all inlet openings leading to the inlet opening of the filters is significantly reduced which has been found nearly to eliminate the risk of blocking of the filter by directly pressing the contents of the bag against the inlet opening(s) of the filter e.g. when a lying person turns. e.g. in bed.

Figure 2:
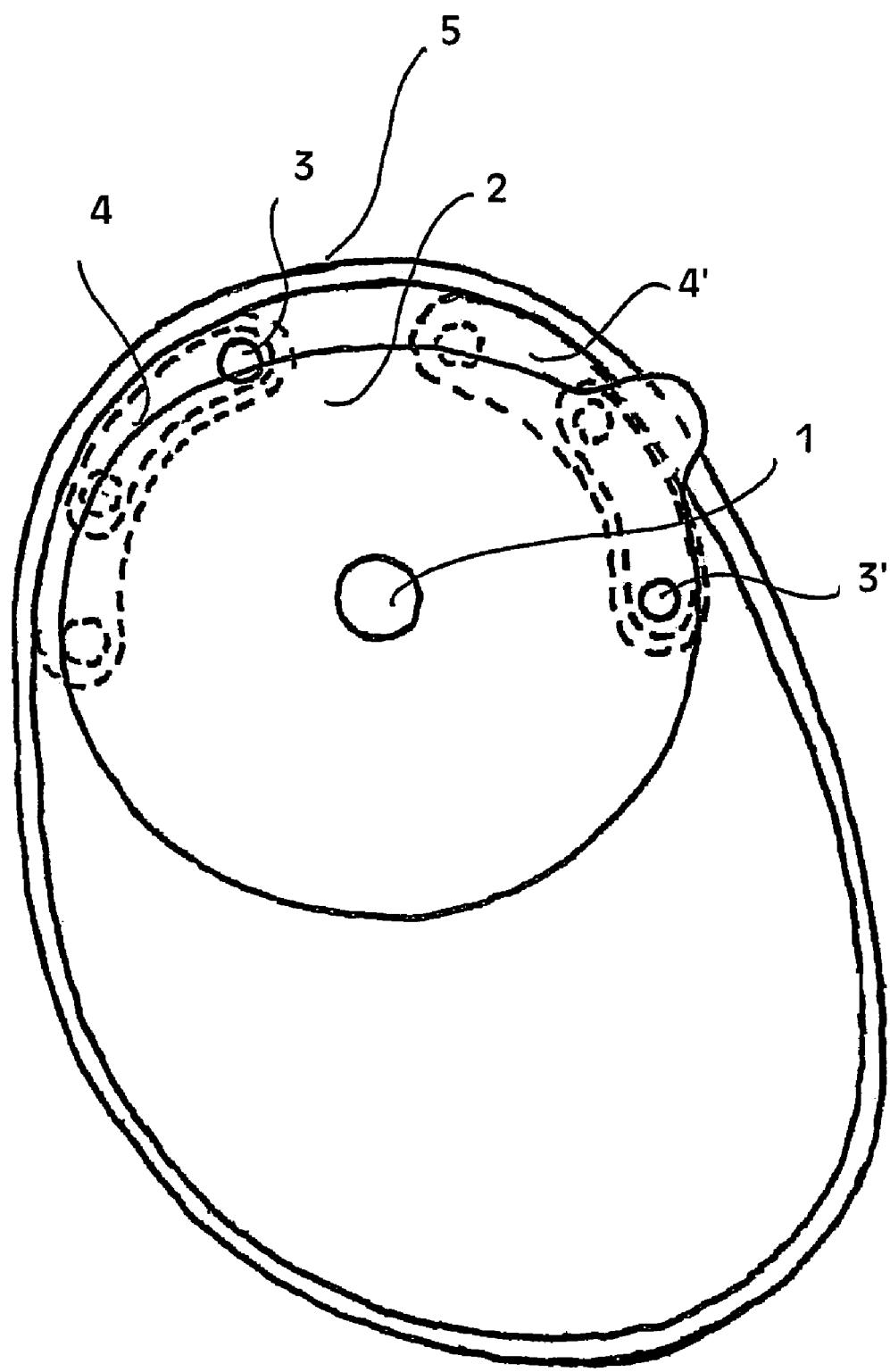
FIG. 2 shows another embodiment of an ostomy appliance of the invention.

FIG. 2 shows another embodiment of an ostomy appliance of the invention corresponding to the embodiment of FIG. 1 apart from that all the top 5 of the bag has a border line being a part of a circle and the filters having outer border lines being part of a circle having essentially the same radius allowing a localisation of the filter very near to the inner rim of the bag.

Figure 3:
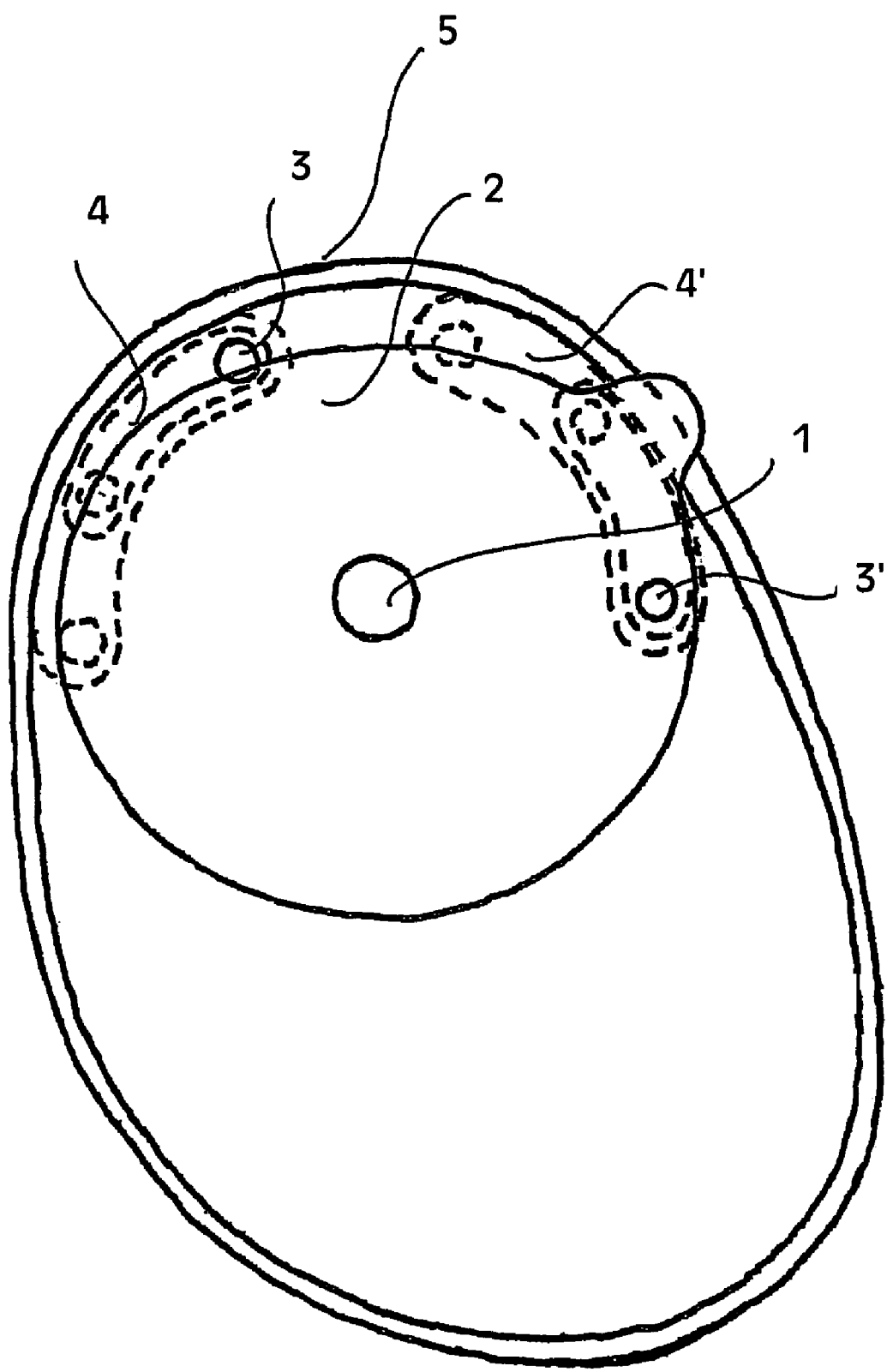
FIG. 3 shows a third embodiment of an ostomy appliance of the invention.

FIG. 3 shows further embodiment of an ostomy appliance of the invention corresponding the embodiment shown in FIG. 2 wherein the two filter devices are located end to end at the top of the bag.

Figure 4:
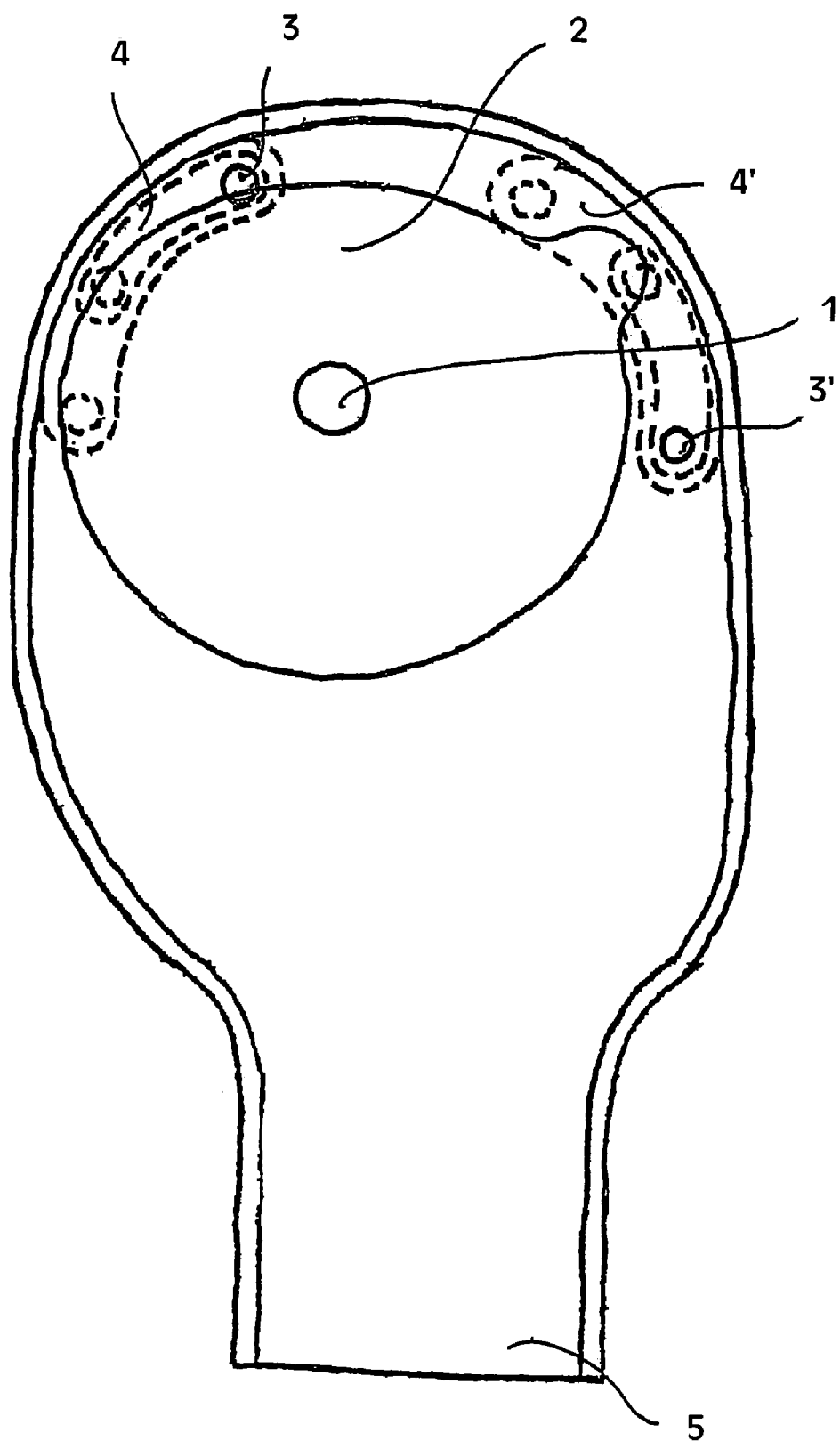
FIG. 4 shows a fourth embodiment of an ostomy appliance of the Invention.

FIG. 4 shows yet another embodiment of an ostomy appliance of the invention corresponding the embodiment shown in FIG. 1 wherein the appliance is in the form of an open bag having a closable open end 5 enabling an emptying of the bag without detaching the same. The bag may be closed in a manner known per se using closing means known per se for closing open ostomy appliances.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention is:

1. An ostomy appliance comprising a front wall and a rear wall of flexible material forming a bag, the rear wall having a waste opening into the bag by which waste material can enter an inner space of the bag, said bag having two or more vents through which gas may escape from the bag, each vent being covered by a separate filter device, each filter device being provided with a respective gas inlet opening in communication with the inner space of the bag and a respective filter body, and a respective outlet opening in communication with said filter body and a respective one of said vents so that in use gas flows through the filter device from the inlet opening through the filter body to the outlet opening, such gas flow being confined to said filter body, said two separate filter devices being provided in one of said walls and the respective inlet openings of said two filter devices being located at opposite sides of a vertical center line of said bag, less than three centimeters from a border of the bag and spaced from one another at an angle of at least about 45 degrees along radii of a circle of reference having a perimeter concentric with the waste opening of the bag.

2. The ostomy appliance as claimed in claim 1, wherein the filter devices have border lines being a part of a circle.

3. The ostomy appliance as claimed in claim 2, wherein at least a part of a top of the bag where the filters are secured has a border line that is part of a circle having the same diameter as that of the filter devices.

4. The ostomy appliance as claimed in claim 2, wherein a top of the bag has a border line that is a part of a circle having the same diameter as that of the filter devices.

5. The ostomy appliance as claimed in claim 2, wherein the separate filter devices are located end to end at a top of the bag.

6. An ostomy appliance comprising a front wall and a rear wall of flexible material forming a bag, the rear wall having a waste opening into the bag by which waste material can enter an inner space of the bag, said bag having two or more vents through which gas may escape from the bag, each vent being covered by a separate filter device, each filter device being provided with a respective gas inlet opening in communication with the inner space of the bag and a respective filter body, and a respective outlet opening in communication with said filter body and a respective one of said vents so that in use gas flows through the filter device from the inlet opening through the filter body to the outlet opening, such gas flow being confined to said filter body, each of the walls of the ostomy appliance being provided with at least one vent and a separate associated filter device, the inlet openings of said associated filter devices being located at opposite sides of a vertical center line of said bag, less than three centimeters from a border of the bag and spaced from one another at an angle of at least about 45 degrees along radii of a circle of reference having a perimeter concentric with the waste opening of the bag.

7. An ostomy appliance comprising a front wall and a rear wall of flexible material forming a bag, the rear wall having a waste opening into the bag by which waste material can enter an inner space of the bag, said bag having at least a first vent and a second vent through which gas may escape from the bag, a first filter device covering said first vent and a second filter device covering said second vent, said first and second filter devices being independent from one another, said first filter device being provided with a first gas inlet opening, a first filter body and a first gas outlet opening, said first gas inlet opening being in communication with the inner space of the bag and said first filter body, and said first outlet opening being in communication with said first filter body and said first vent so that in use gas flows from the inner space of the bag, through the first inlet opening through the first filter body to the first outlet opening and out the first vent, said second filter device being provided with a second gas inlet opening, a second filter body and a second gas outlet opening, said second gas inlet opening being in communication with the inner space of the bag and said second filter body, and said second outlet opening being in communication with said second filter body and said second vent so that in use gas flows from the inner space of the bag, through the second inlet opening through the second filter body to the second outlet opening and out the second vent, said first and second inlet openings of the filter devices being located at opposite sides of a vertical center line of said bag, less than three centimeters from a border of the bag and spaced from one another at an angle of at least about 45 degrees along radii of a circle of reference having a perimeter concentric with the waste opening of the bag.

8. The ostomy appliance as set forth in claim 7, wherein said first and second vents are both in one of said walls.

9. The ostomy appliance as set forth in claim 7, wherein said first vent is in said front wall and said second vent is in said rear wall.

10. The ostomy appliance as claimed in claim 7, wherein the first and second filter devices are located end to end at a top of the bag.

11. The ostomy appliance as claimed in claim 7, wherein the filter devices have border lines being a part of a circle.

12. The ostomy appliance as claimed in claim 11, wherein at least a part of a top of the bag where the filters are secured has a border line that is part of a circle having the same diameter as that of the filter devices.

13. The ostomy appliance as claimed in claim 11, wherein a top of the bag has a border line that is a part of a circle having the same diameter as that of the filter devices.

14. The ostomy appliance as claimed in claim 11, wherein the separate filter devices are located end to end at a top of the bag.

15. The ostomy appliance as claimed in claim 6, wherein the first and second filter devices are spaced from one another so that, although on separate walls, they are located end to end at a top of the bag.

16. The ostomy appliance as claimed in claim 6, wherein the filter devices have border lines being a part of a circle.

17. The ostomy appliance as claimed in claim 16, wherein at least a part of a top of the bag where the filters are secured has a border line that is part of a circle having the same diameter as that of the filter devices.

18. The ostomy appliance as claimed in claim 16, wherein a top of the bag has a border line that is a part of a circle having the same diameter as that of the filter devices.

* * * * *